United States Patent
Almulhim

(10) Patent No.: US 11,642,206 B1
(45) Date of Patent: May 9, 2023

(54) SYSTEM AND METHOD FOR LAPAROSCOPIC REPAIR OF ABDOMINAL WALL HERNIA USING UMBRELLA MESH

(71) Applicant: KING FAISAL UNIVERSITY, Al-Ahsa (SA)

(72) Inventor: Abdulrahman Saleh Almulhim, Al-Ahsa (SA)

(73) Assignee: KING FAISAL UNIVERSITY, Al-Ahsa (SA)

(*) Notice: Subject to any disclaimer, the term of this patent is extended or adjusted under 35 U.S.C. 154(b) by 0 days.

(21) Appl. No.: 17/989,632

(22) Filed: Nov. 17, 2022

(51) Int. Cl.
*A61F 2/00* (2006.01)
*A61B 1/313* (2006.01)
*A61B 17/00* (2006.01)

(52) U.S. Cl.
CPC .......... *A61F 2/0063* (2013.01); *A61B 1/313* (2013.01); *A61B 2017/00871* (2013.01); *A61F 2002/0072* (2013.01)

(58) Field of Classification Search
CPC ............ A61F 2/0063; A61F 2002/0072; A61F 2002/0068; A61F 2002/30062; A61F 2002/30092; A61F 2220/0016; A61F 2210/0004; A61F 2210/0019; A61F 2230/0006; A61B 17/00234; A61B 17/0057; A61B 17/064; A61B 17/068; A61B 2017/00579; A61B 2017/00597; A61B 2017/0061; A61B 2017/00867; A61B 2017/00871
USPC .......................................................... 606/151
See application file for complete search history.

(56) References Cited

U.S. PATENT DOCUMENTS

| | | | |
|---|---|---|---|
| 5,397,331 A * | 3/1995 | Himpens | A61B 17/064 606/232 |
| 9,687,332 B2 * | 6/2017 | Sholev | A61F 2/0063 |
| 2005/0256532 A1 * | 11/2005 | Nayak | A61B 17/0057 606/151 |

(Continued)

FOREIGN PATENT DOCUMENTS

| CN | 209734230 U | 12/2019 |
|---|---|---|
| CN | 213665974 U | 7/2021 |

OTHER PUBLICATIONS

Al-Hawaz, "Umbrella Mesh Versus Mayo's Repair in Primary Umbilical Hernia", Basrah Journal of Surgery (2002), vol. 8, Iss. 2, 4 pages.

(Continued)

*Primary Examiner* — Mohamed G Gabr
(74) *Attorney, Agent, or Firm* — Nath, Goldberg & Meyer; Richard C. Litman

(57) ABSTRACT

The system and method for laparoscopic repair of abdominal wall hernia using umbrella mesh includes an umbrella mesh having a substantially circular mesh attached to an umbrella-like frame having a plurality of radially spaced spokes resiliently mounted at a hub, the spokes being hollow and housing helical tacks. The umbrella mesh is folded and mounted on an umbrella load cartridge. The cartridge may be loaded on the distal end of a pistol-grip laparoscopic instrument having a rotary control for orienting the mesh over the weakened area, a mesh release handle for gradually opening and releasing the mesh, and a firing handle for firing helical tacks from the spokes for fastening the mesh to the supporting abdominal wall.

11 Claims, 5 Drawing Sheets

(56) References Cited

U.S. PATENT DOCUMENTS

| | | | |
|---|---|---|---|
| 2007/0185506 A1* | 8/2007 | Jackson | A61F 2/0063 606/151 |
| 2008/0140203 A1* | 6/2008 | Davis | A61F 2/442 623/17.13 |
| 2009/0204129 A1* | 8/2009 | Fronio | A61F 2/0063 606/151 |
| 2010/0069930 A1* | 3/2010 | Roslin | A61B 17/0057 606/151 |
| 2010/0179576 A1* | 7/2010 | Halevy | A61F 2/0063 606/151 |
| 2012/0016409 A1* | 1/2012 | Sherwinter | A61F 2/0063 606/213 |
| 2013/0035704 A1* | 2/2013 | Dudai | A61F 2/0063 606/151 |

OTHER PUBLICATIONS

Abhishek et al., "Laparoscopic Umbilical Hernia Repair: Technique Paper", ISRN Minimally Invasive Surgery (2012), vol. 2012, Article ID 906405, 4 pages.

Kitamura et al., "Suture Versus Tack Fixation of Mesh in Laparoscopic Umbilical Hernia Repair", JSLS (2013), vol. 17, pp. 560-564.

\* cited by examiner

SYSTEM AND METHOD FOR LAPAROSCOPIC REPAIR OF ABDOMINAL WALL HERNIA USING UMBRELLA MESH

BACKGROUND

1. Field

The disclosure of the present patent application relates to hernia repair, and particularly to a system and method for laparoscopic repair of abdominal wall hernia using umbrella mesh.

2. Description of the Related Art

In abdominal wall hernias, the muscles of the abdomen become weak, and the intestine, fat, or other tissue or organ may protrude through the weakened area, causing a lump or bulge that can be seen or palpated. Left untreated, the hernia may become larger and eventually become strangulated, with increasing pain and risk of rupture. There are several different types of abdominal wall hernia, including epigastric hernias (between the breastbone and the umbilicus), incisional hernias (from prior surgeries), umbilical hernias, and others. Quite frequently the appropriate treatment of choice is surgery, which may be open surgery or minimally invasive or laparoscopic surgery. Whichever form of surgery is elected, the abdominal tissue and repair may be supported by a mesh. In recent years, laparoscopic surgery for repair of abdominal hernias has become more popular due to smaller incisions, less pain, less inpatient time, and shorter recovery times. Although great strides have been made in improving laparoscopic repair of abdominal wall hernias, there is still a need for improvements that will reduce the number of incisions, operative time in surgery, pain, and reduced postoperative recovery time. Thus, a system and method for laparoscopic repair of abdominal wall hernia using umbrella mesh solving the aforementioned problems is desired.

SUMMARY

The system and method for laparoscopic repair of abdominal wall hernia using umbrella mesh includes an umbrella mesh having a substantially circular mesh attached to an umbrella-like frame having a plurality of radially spaced spokes resiliently mounted at a hub, the spokes being hollow and housing helical tacks. The umbrella mesh is folded and mounted on an umbrella load cartridge. The cartridge may be loaded on the distal end of a pistol-grip laparoscopic instrument having a rotary control for orienting the mesh over the weakened area, a mesh release handle for gradually opening and releasing the mesh, and a firing handle for firing helical tacks from the spokes for fastening the mesh to the supporting abdominal wall.

In use, the laparoscopic instrument is used to insert the umbrella load cartridge through a trocar port into the abdominal cavity (the cavity being insufflated with carbon dioxide gas to separate the abdominal wall from the contents of the abdomen); the protruding organ or tissue is moved away from the weakened area of the abdominal wall; the mesh release handle gradually unloads the umbrella mesh from the cartridge, the rotary control orienting the ends of the spokes to desired anchor points in stronger tissue of the abdominal wall surrounding the weakened area of the abdominal wall as the umbrella mesh resiliently opens; when the umbrella mesh completely opens, the firing handle fires the helical tacks from the spokes to fasten the mesh to the abdominal wall, covering the weakened area with the mesh support; barrel of the laparoscopic instrument is withdrawn from the abdominal cavity through the trocar port; and the laparoscopic incisions are closed as needed.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The system and method for laparoscopic repair of abdominal wall hernia using umbrella mesh includes an umbrella mesh having a substantially circular mesh attached to an umbrella-like frame having a plurality of radially spaced spokes resiliently mounted at a hub, the spokes being hollow and housing helical tacks. The umbrella mesh is folded and mounted on an umbrella load cartridge. The cartridge may be loaded on the distal end of a pistol-grip laparoscopic instrument having a rotary control for orienting the mesh over the weakened area, a mesh release handle for gradually opening and releasing the mesh, and a firing handle for firing helical tacks from the spokes for fastening the mesh to the supporting abdominal wall.

Figure 3:
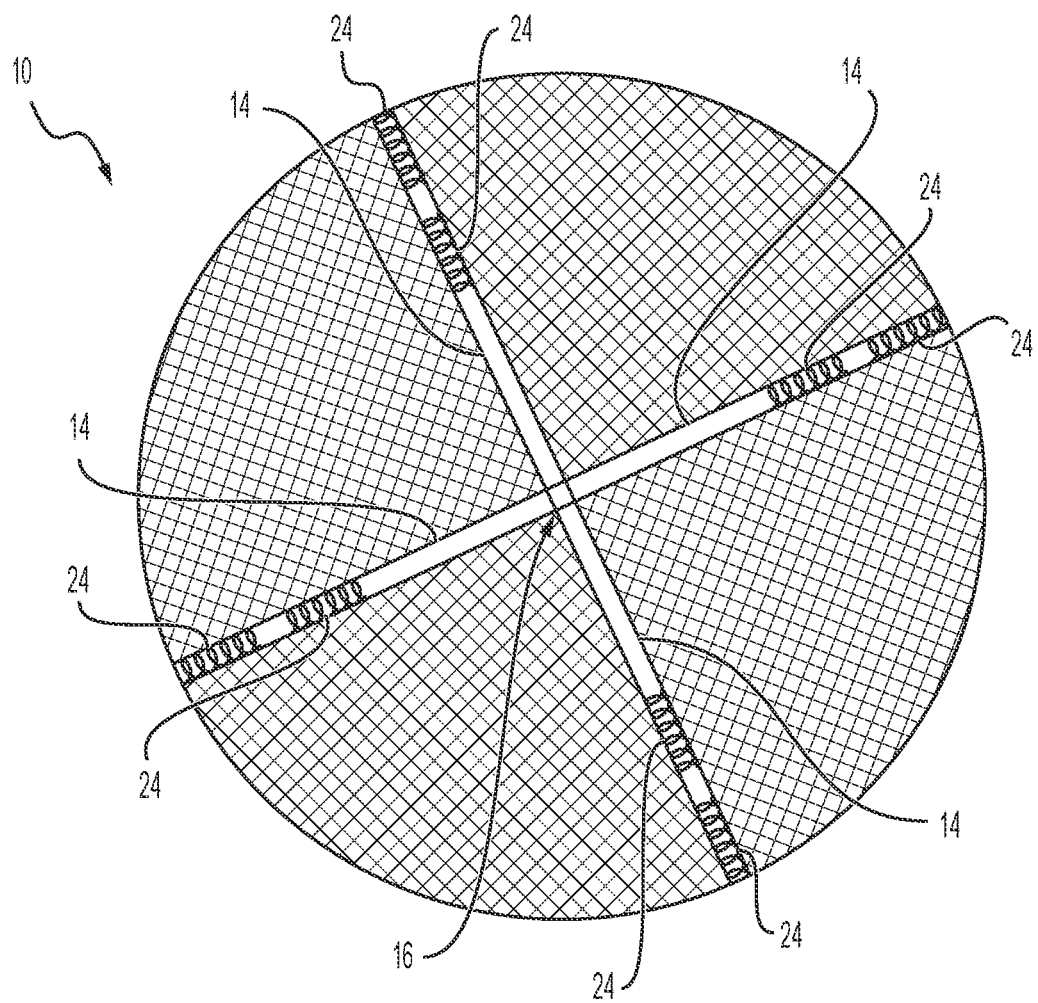
FIG. 3 is a schematic perspective view showing the umbrella mesh of FIG. 1 in a fully open configuration.

FIG. 3 shows the umbrella mesh assembly 10 in its normal fully extended circular configuration. The assembly 10 includes a circular mesh 12 of woven polymer fibers. The mesh 12 may be made of biocompatible fibers commonly known in the art of hernia repair meshes, such as a layer of polypropylene mesh bonded to a layer of polytetrafluoroethylene (PTFE) mesh. The mesh 12 is mounted on a plurality of resilient, radially spaced spokes 14 joined together at a central hub area 16. FIG. 3 shows four such spokes 14 spaced apart 90° radially, although the umbrella mesh 10 may have more spokes 14 spaced closer together radially if needed to support a larger mesh. The spokes 14 may be made of a resilient material, such as spring steel or a resilient biocompatible plastic or polymer.

Figure 1:
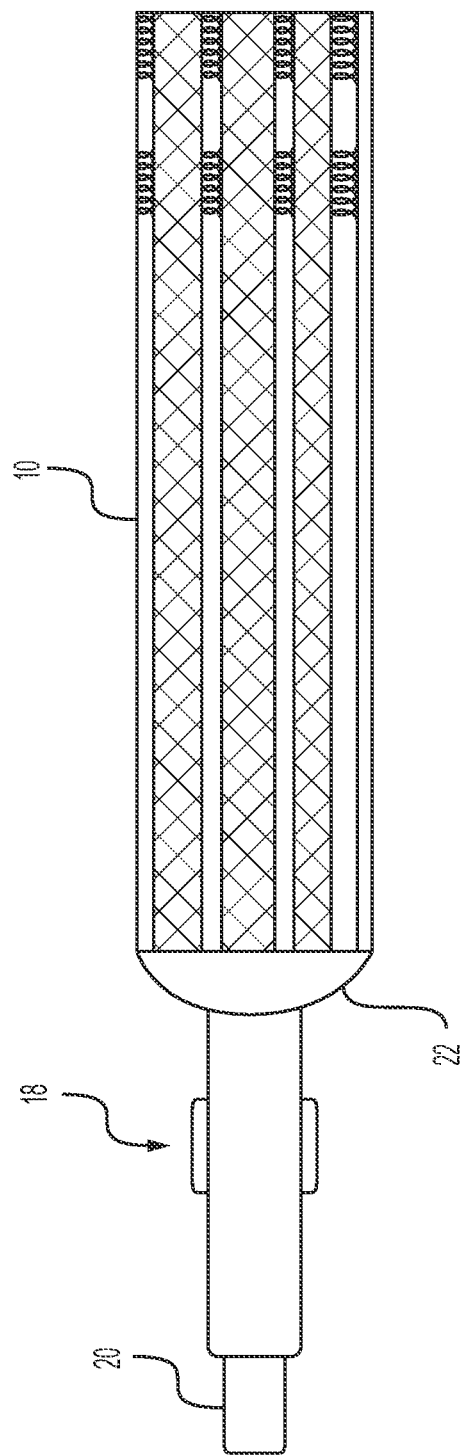
FIG. 1 is a perspective view of an umbrella mesh cartridge having a folded umbrella mesh mounted thereon.
Figure 2:
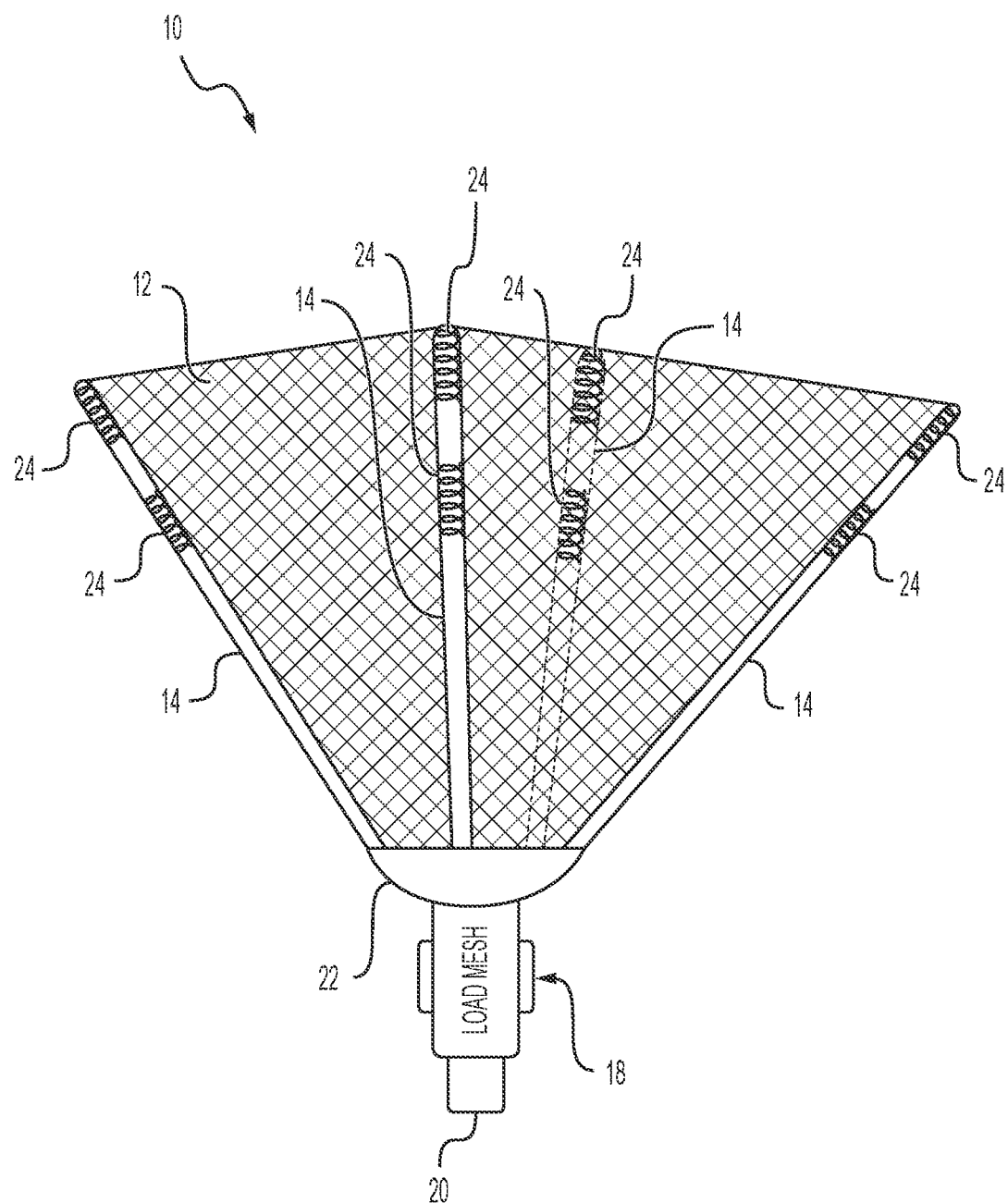
FIG. 2 is a perspective view of the umbrella mesh of FIG. 1 in a partially open configuration.

As shown in FIGS. 1 and 2, the spokes 14 may be bent near the central hub 16 to fold the umbrella mesh 10 into a folded or retracted position with the spokes 14 closely adjacent each other and perpendicular to the central hub area 16 for mounting on an umbrella load cartridge 18. The umbrella load cartridge 18 may have a mounting lug 20 at one end and a dome-shaped spoke engagement member 22 at its opposite end engaging a proximal end of the spokes 14 to keep the umbrella mesh 10 folded until the mesh 10 is deployed. As shown schematically in FIGS. 1-3, the spokes 14 are tubular and carry helical tacks 24 or tacker mechanisms that will be used to fasten the umbrella mesh 10 to the abdominal wall when the mesh is properly positioned. Helical tacks 24 made of titanium and tacker mechanisms for fastening hernia meshes to supporting healthy tissue are well known in laparoscopic surgery and need not be described further.

Figure 4:
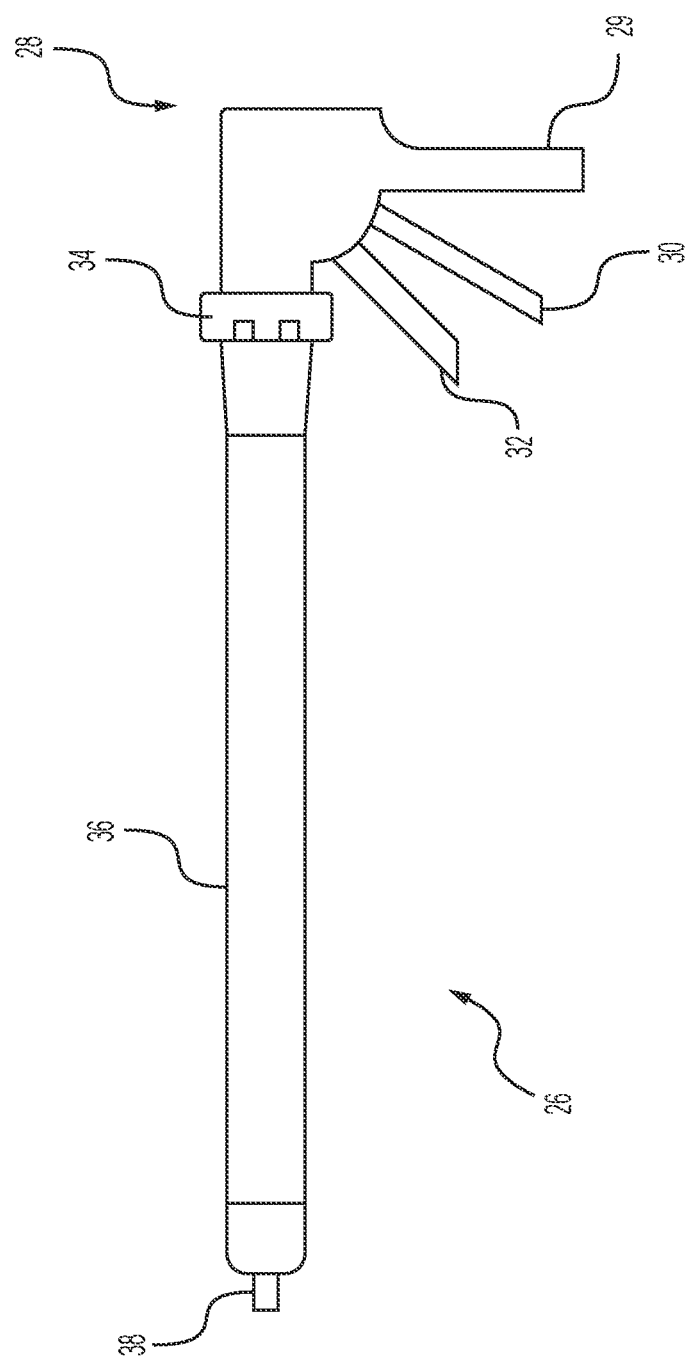
FIG. 4 is a side view of a laparoscopic instrument for installing the umbrella mesh of FIG. 1.
Figure 5:
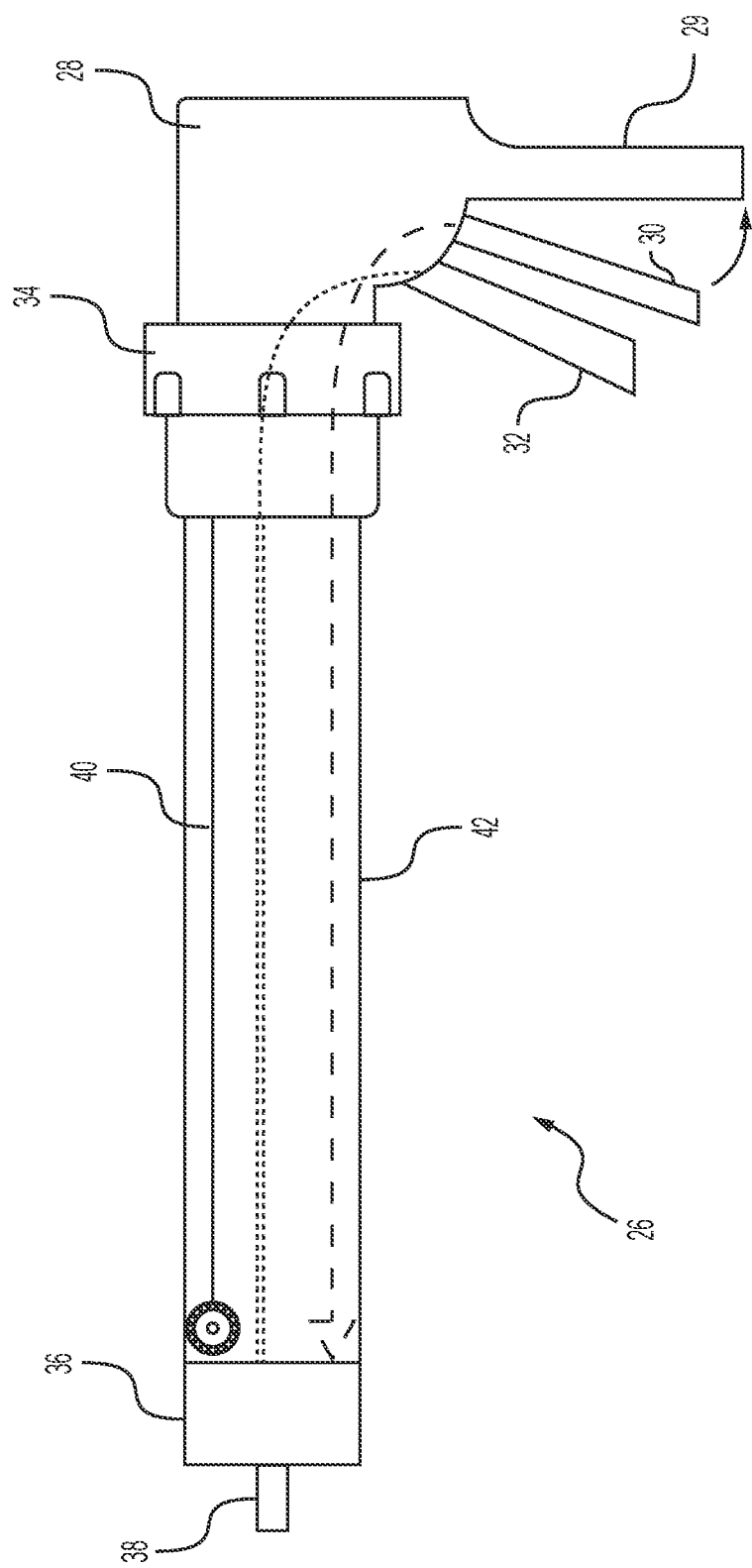
FIG. 5 is a schematic side view of the laparoscopic instrument of FIG. 4 showing the instrument controls.

FIGS. 4 and 5 show a laparoscopic instrument 26 for fixing the umbrella mesh 10 to the patient's abdominal wall to cover the herniated area and support the organs and tissue that would otherwise bulge through the herniated area before it heals. As shown in FIG. 4, the laparoscopic instrument 26 has a pistol-grip handle 28 having a fixed hand grip 29, a mesh trigger 30 for opening the umbrella mesh 10, and a tacker firing trigger 32 for ejecting the helical tacks 24 from the spokes 14 to fasten the umbrella mesh 10 to healthy tissue surrounding the herniated area to fasten the mesh 10 to the abdominal wall. The distal end of the handle 28 has a rotary control 34 mounted thereon. When the rotary control 34 is rotated, it pulls the umbrella mesh 10 in up to a 90° arc to position the ends of the spokes 14 in an optimum location for fastening the mesh 10 to healthy abdominal tissue to cover the herniated area while it heals and support internal organs and tissues. A barrel 36 extends from the handle 28 and terminates in a socket 38 or other connector for holding the umbrella load cartridge 18 on the instrument 18 while the barrel 36 is inserted through a trocar port into the abdominal cavity and manipulated to position and fasten the umbrella mesh 10.

As shown schematically in FIG. 5, a mesh control rod 40 extends through the barrel 36 between the rotary control 34 at the distal end of the handle 28 and the end of the barrel 36 connected to the umbrella load cartridge 18. Similarly, a tacker control rod 42 extends through the barrel 36 between the tacker firing trigger 32 and the end of the barrel 36 connected to the umbrella load cartridge 18.

The method for laparoscopic repair of abdominal wall hernia folding the umbrella mesh 10; loading the folded umbrella mesh onto an umbrella load cartridge 18; mounting the umbrella load cartridge 18 onto the barrel 36 of the laparoscopic instrument; inserting the umbrella load cartridge 18 through a trocar port into the abdominal cavity (the cavity being insufflated with carbon dioxide gas to separate the abdominal wall from the contents of the abdomen); repairing the weakened area of the herniated abdominal wall; moving the protruding organ or tissue is away from the weakened area of the abdominal wall; operating the mesh trigger 30 or mesh release handle to gradually unload the umbrella mesh 10 from the cartridge 18; using the rotary control 34 to orient the ends of the spokes 14 to desired anchor points in stronger tissue of the abdominal wall surrounding the weakened area of the abdominal wall as the umbrella mesh 10 resiliently opens; when the umbrella mesh 10 completely opens, using the tacker firing trigger 32 or firing handle to fire the helical tacks 24 from the spokes 14 to fasten the mesh 10 to the abdominal wall, covering the weakened area with the mesh support; withdrawing the barrel 36 of the laparoscopic instrument 26 from the abdominal cavity through the trocar port; and closing the laparoscopic incisions as needed.

It is to be understood that the system and method for laparoscopic repair of abdominal wall hernia using umbrella mesh is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A system for laparoscopic repair of abdominal hernia using umbrella mesh, comprising:
    an umbrella mesh having:
        a plurality of resilient radially spaced tubular spokes joined at a central hub area, the spokes being foldable to a folded configuration having the spokes substantially parallel to each other and perpendicular to the central hub area, the spokes resiliently expanding to an unfolded configuration defining a substantially planar mesh support; and
        a mesh of biocompatible woven polymer fibers attached to the spokes;
    an elongated umbrella load cartridge having a mounting lug at a first end and a dome-shaped spoke engagement member at an opposing second end, the spoke engaging member engaging a proximal end of the spokes to keep the umbrella mesh in the folded configuration until the umbrella mesh is deployed;
    a plurality of helical tacks loaded in the spokes of the umbrella mesh;
    a laparoscopic instrument for fixing the umbrella mesh to a patient's abdominal wall to cover a herniated area of the abdominal wall, the laparoscopic instrument having:
        a pistol-grip handle having a fixed hand grip, a mesh trigger for opening the umbrella mesh, and a tacker firing trigger for selectively ejecting the helical tacks from the umbrella mesh spokes to tack the umbrella mesh to healthy tissue surrounding the herniated area in the abdominal wall;
        a hollow barrel extending from the pistol-grip handle, the barrel housing a mesh control rod and tacker control rod; and
        a connector mounted on a distal end of the barrel, the connector receiving the mounting lug of the umbrella load cartridge to mount the umbrella load cartridge on the laparoscopic instrument.

2. The system for laparoscopic repair of abdominal hernia according to claim 1, wherein said spokes are made of spring steel.

3. The system for laparoscopic repair of abdominal hernia according to claim 1, wherein said plurality of spokes consists of four spokes.

4. The system for laparoscopic repair of abdominal hernia according to claim 3, wherein said spokes are radially spaced 90° apart.

5. The system for laparoscopic repair of abdominal hernia according to claim 1, wherein said umbrella mesh is circular.

6. The system for laparoscopic repair of abdominal hernia according to claim 1, wherein said mesh of biocompatible woven polymer fibers comprises a bilayer composite including a layer of polypropylene bonded to a layer of polytetrafluoroethylene.

7. The system for laparoscopic repair of abdominal hernia according to claim 1, wherein said helical tacks are made from titanium.

8. The system for laparoscopic repair of abdominal hernia according to claim 1, wherein said laparoscopic instrument further comprises a rotary control disposed between said handle and said barrel for rotating said umbrella mesh while positioning said umbrella mesh over the herniated area of the abdominal wall.

9. A method for laparoscopic repair of abdominal hernia using umbrella mesh using the system according to claim 1, comprising the steps of:
    folding the umbrella mesh;
    loading the folded umbrella mesh onto the umbrella load cartridge;
    mounting the umbrella load cartridge onto the barrel of the laparoscopic instrument;
    inserting the umbrella load cartridge through a trocar port into the abdominal cavity, the cavity being insufflated with carbon dioxide gas to separate the abdominal wall from contents of the abdomen;

moving a protruding organ or tissue is away from the herniated area of the abdominal wall;

operating the mesh trigger to gradually unload the umbrella mesh from the umbrella load cartridge; using a rotary control mounted between the handle and the barrel of the laparoscopic instrument to orient ends of the spokes to desired anchor points in stronger tissue of the abdominal wall surrounding the herniated area of the abdominal wall as the umbrella mesh resiliently opens;

when the umbrella mesh completely opens, using the tacker firing trigger to fire the helical tacks from the spokes to fasten the mesh to the abdominal wall, covering the herniated area with the mesh.

10. The method for laparoscopic repair of abdominal hernia according to claim 9, further comprising the step of withdrawing the barrel of the laparoscopic instrument from the abdominal cavity through the trocar port.

11. The method for laparoscopic repair of abdominal hernia according to claim 10, further comprising the step of closing laparoscopic incisions as needed.

\* \* \* \* \*